(12) United States Patent
Maliverney et al.

(10) Patent No.: US 8,431,750 B2
(45) Date of Patent: Apr. 30, 2013

(54) PREPARATION OF HYDROXYAROMATIC ALDEHYDES

(75) Inventors: Christian Maliverney, Saint-Julien-sur-Bibost (FR); Jean-Christophe Bigouraux, Dargoire (FR); Laurent Garel, Lyons (FR)

(73) Assignee: Rhodia Operations, Aubervilliers (FR)

( * ) Notice: Subject to any disclaimer, the term of this patent is extended or adjusted under 35 U.S.C. 154(b) by 171 days.

(21) Appl. No.: 12/663,344

(22) PCT Filed: Jun. 3, 2008

(86) PCT No.: PCT/EP2008/056850
§ 371 (c)(1),
(2), (4) Date: Aug. 24, 2011

(87) PCT Pub. No.: WO2008/148760

PCT Pub. Date: Dec. 11, 2008

(65) Prior Publication Data

US 2011/0306802 A1    Dec. 15, 2011

(30) Foreign Application Priority Data

Jun. 6, 2007 (FR) .......... 07 04043

(51) Int. Cl.
*C07C 45/39* (2006.01)
(52) U.S. Cl.
USPC .......... 568/432; 568/435
(58) Field of Classification Search .......... 568/432, 568/435
See application file for complete search history.

(56) References Cited

U.S. PATENT DOCUMENTS 6,753,441 B1 * 6/2004 Jouve et al. .......... 560/60
2004/0267023 A1  12/2004 Goehring et al.

FOREIGN PATENT DOCUMENTS

DE       289516 A5    5/1991

OTHER PUBLICATIONS

Nalwaya et al., "Kinetics studies on oxidation of mandelic acid by chromium (VI) catalyzed by MN(II)", Chemical Abstract Service, 2003:779352, Ohio, XP 002468472.

* cited by examiner

*Primary Examiner* — Sikarl Witherspoon
(74) *Attorney, Agent, or Firm* — SNR Denton US LLP

(57) ABSTRACT

Hydroxyaromatic aldehydes are prepared by oxidation of a corresponding mandelic derivative carried out in a basic medium and in the presence of a catalytic system containing at least two metal elements.

24 Claims, No Drawings

PREPARATION OF HYDROXYAROMATIC ALDEHYDES

CROSS-REFERENCE TO PRIORITY/PCT APPLICATIONS

This application is a National Stage of PCT/EP2008/056850, filed Jun. 3, 2008, and designating the United States (published in French on Dec. 11, 2008, as WO 2008/148760 A2), which claims priority under 35 U.S.C. §119 of FR 07/004,043 filed Jun. 6, 2007, each hereby expressly incorporated by reference in its entirety and each assigned to the assignee hereof.

The subject matter of the present invention is a process for the preparation of a hydroxyaromatic aldehyde by oxidation of a corresponding mandelic derivative.

The invention relates more particularly to the preparation of 4-hydroxy-3-methoxybenzaldehyde and 3-ethoxy-4-hydroxybenzaldehyde, known respectively as "vanillin" and "ethyl vanillin", by oxidation respectively of 4-hydroxy-3-methoxymandelic acid and 3-ethoxy-4-hydroxymandelic acid.

Vanillin is obtained from natural sources, such as lignin or ferulic acid, but a significant portion of vanillin is produced chemically.

Numerous diverse and varied preparation methods are described in the literature [KIRK-OTHMER, Encyclopedia of Chemical Technology, 24, pp. 812-825, 4th edition (1997)] and several of them start from guaiacol or 2-methoxyphenol.

Thus, mention may be made of the preparation of vanillin according to the Reimer-Tiemann reaction, which consists in reacting guaiacol and chloroform in the presence of potassium hydroxide. The formation of resin is a disadvantage of this preparation method.

More recently, a description has been given in EP-A-0 773 919 in particular of the preparation of vanillin according to a process which consists in reacting formaldehyde and guaiacol in the presence of sodium hydroxide, resulting in a mixture comprising o-hydroxymethylguaiacol (OMG), p-hydroxymethylguaiacol (PMG) and 4,6-di(hydroxymethyl) guaiacol (DMG), in then oxidizing said mixture with oxygen in the presence of a palladium catalyst and of a bismuth catalyst and in subsequently eliminating, in the oxidation products comprising it, the carboxyl group situated in the ortho position, thus making it possible to obtain vanillin with a good reaction yield.

Furthermore, there exists a completely different route for access to vanillin which consists in reacting guaiacol and glyoxylic acid in basic medium, resulting in 4-hydroxy-3-methoxymandelic acid, in oxidizing the condensate in the air and in then releasing vanillin from the reaction medium by acidification.

An illustration of this type of process is described in U.S. Pat. No. 2,062,205, which relates to a process for the preparation of protocatechualdehyde ethers which consists in reacting an o-alkoxyphenol and a soluble salt of glyoxylic acid in alkaline solution and in subsequently treating the product thus obtained with a mild oxidizing agent, such as copper oxide CuO, lead dioxide $PbO_2$, manganese oxide $MnO_2$, cobalt oxide $Co_3O_4$, mercury oxide HgO or silver oxide $Ag_2O$.

With respect to said process, the Applicant Company provides an improvement to the oxidation stage which makes it possible to obtain vanillin with a good reaction yield and an improved selectivity.

More specifically, a subject matter of the present invention is a process for the preparation of a hydroxyaromatic aldehyde by oxidation of the corresponding mandelic derivative in basic medium, characterized in that the oxidation of said mandelic derivative is carried out in the presence of a catalytic system comprising at least two metal elements $M_1$ and $M_2$ chosen from the group formed by copper, nickel, cobalt, iron and manganese.

It has been found, surprisingly, that vanillin can be obtained by oxidation of 4-hydroxy-3-methoxymandelic acid in basic medium with a good reaction yield and in particular an improved selectivity provided that use is made of a catalytic system comprising at least two metal elements chosen from the group defined according to the present invention.

To date, it has never been described that the use of such a combination of metal elements makes it possible to improve the performance of the reaction.

In the account which follows of the present invention, "hydroxyaromatic aldehyde" is understood to mean an aromatic compound in which at least two hydrogen atoms directly bonded to the aromatic nucleus are replaced, one by a hydroxyl group and the other by a formyl group, and "aromatic compound" is understood to mean the classical notion of aromaticity as defined in the literature, in particular by Jerry March, Advanced Organic Chemistry, 4th edition, John Wiley and Sons, 1992, pp. 40 et seq.

"Mandelic derivative" is understood to mean an aromatic compound in which at least two hydrogen atoms directly bonded to the aromatic nucleus are replaced, one by a hydroxyl group and the other by a glycolic group of formula —CHOH—COOH.

The expression "mandelic acid" denotes phenylglycolic acid of formula $C_6H_5$—CHOH—COOH.

One substrate involved in the process of the invention is an aromatic compound carrying at least one hydroxyl group and one glycolic group and it is also referred to subsequently as "mandelic substrate".

It should be noted that the aromatic nucleus can also carry one or more other substituents. Generally, several substituents defines less than four substituents per aromatic nucleus.

Any substituent can be present insofar as it is compatible with the reaction envisaged. Examples of substituents are given below but the list is in no way limiting.

Thus, the process of the invention is well suited to being applied to mandelic substrates corresponding to the following formula (I):

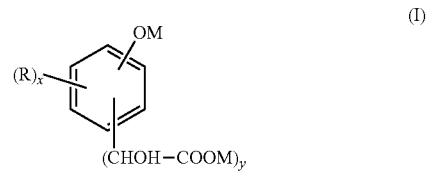

in said formula (I):
M represents a hydrogen atom and/or a metal cation of group Ia of the Periodic Table of the Elements or an ammonium cation,
R represents a hydrogen atom or one or more identical or different substituents,
y is a number equal to 1 or 2,
x, the number of substituents on a ring, is a number less than or equal to 4,
when x is greater than 1, two R groups placed on two adjacent carbon atoms can, together and with the carbon atoms which carry them, form a saturated, unsaturated or aromatic ring having from 5 to 7 atoms and optionally comprising one or more heteroatoms.

In formula (I), the R groups, which are identical or different, represent a hydrogen atom, an alkyl, alkenyl, alkoxy, hydroxyalkyl, alkoxyalkyl, cycloalkyl, aryl or arylalkyl group, a hydroxyl group, a nitro group, a halogen atom, a halo- or perhaloalkyl group, a carboxyl group or an amino group which is unsubstituted or substituted by one or two alkyl or phenyl groups.

In the formula (I), when x is greater than 1, two R groups placed on two adjacent carbon atoms can be bonded to one another via an alkylene, alkenylene or alkenyldiene group having from 3 to 5 carbon atoms in order to form a saturated, unsaturated or aromatic ring having from 5 to 7 atoms, it being possible for one or more (preferably 2 or 3) carbon atoms to be replaced by a heteroatom, preferably oxygen.

In the context of the invention, "alkyl" is understood to mean a linear or branched hydrocarbon chain having from 1 to 15 carbon atoms and preferably from 1 or 2 to 10 carbon atoms.

"Alkoxy" is understood to mean an alkyl-O— group in which the term alkyl has the meaning given above. Preferred examples of alkoxy groups are the methoxy or ethoxy groups.

"Alkenyl" is understood to mean a linear or branched hydrocarbon group having from 2 to 15 carbon atoms and comprising one or more double bonds, preferably 1 to 2 double bonds.

"Cycloalkyl" is understood to mean a cyclic hydrocarbon group comprising from 3 to 8 carbon atoms, preferably a cyclopentyl or cyclohexyl group.

"Aryl" is understood to mean an aromatic mono- or polycyclic group, preferably a mono- or bicyclic group, comprising from 6 to 12 carbon atoms, preferably phenyl or naphthyl.

"Arylalkyl" is understood to mean a linear or branched hydrocarbon group carrying an aromatic monocyclic ring and comprising from 7 to 12 carbon atoms, preferably benzyl.

"Halo- or perhaloalkyl" is understood to mean one of the following groups: —$CX_3$, —$[CX_2]_p$—$CX_3$ or —$C_pH_aF_b$; in said groups, X represents a halogen atom, preferably a chlorine or fluorine atom, p represents a number ranging from 1 to 10, b represents a number ranging from 3 to 21 and a+b=2p+1.

The compounds which are particularly well suited to the implementation of the process of the invention correspond to the formula (I) in which R, which are identical or different, represent:
  a hydrogen atom,
  a hydroxyl group,
  a linear or branched alkyl group having from 1 to 6 carbon atoms, preferably from 1 to 4 carbon atoms, such as methyl, ethyl, n-propyl, isopropyl, n-butyl, isobutyl, sec-butyl or tert-butyl,
  a linear or branched alkenyl group having from 2 to 6 carbon atoms, preferably from 2 to 4 carbon atoms, such as vinyl or allyl,
  a linear or branched alkoxy group having from 1 to 6 carbon atoms, preferably from 1 to 4 carbon atoms, such as the methoxy, ethoxy, n-propoxy, isopropoxy, n-butoxy, isobutoxy, sec-butoxy or tert-butoxy groups,
  a phenyl group,
  a halogen atom, preferably a fluorine, chlorine or bromine atom.

As regards the definition of the other symbols involved in the formula (I), y is equal to 1 or 2, preferably equal to 1, and x is advantageously equal to 0, 1 or 2 and more advantageously equal to 1.

As regards M, it represents a hydrogen atom, a metal cation from group Ia of the Periodic Table of the Elements or an ammonium cation.

In the present text, reference is made below to the Periodic Table of the Elements published in the Bulletin de la Société Chimique de France, No 1 (1966).

Among alkali metal cations, M is preferably sodium or potassium.

Mention may be made, as preferred examples of substrates capable of being employed in the process of the invention, inter alia, of:
4-hydroxy-3-methoxymandelic acid,
3-ethoxy-4-hydroxymandelic acid,
3,4-dihydroxymandelic acid,
2,4-dihydroxymandelic acid,
2-hydroxy-5-methylmandelic acid,
2-hydroxy-5-methoxymandelic acid,
4-hydroxy-3-chloromandelic acid,
4-hydroxy-3-bromomandelic acid,
4-hydroxy-3-fluoromandelic acid,
4-hydroxymandelic acid,
4-hydroxy-3-methoxy-5-methylmandelic acid,
2-hydroxy-2-(1-hydroxynaphth-2-yl)acetic acid.

The present invention applies particularly to the compounds, employed alone or as a mixture, corresponding to the following formulae:

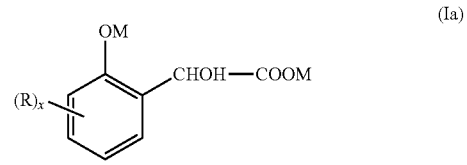
(Ia)

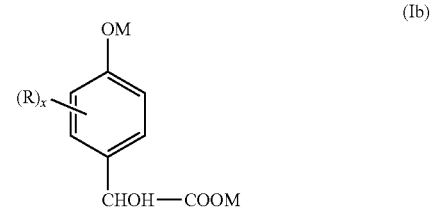
(Ib)

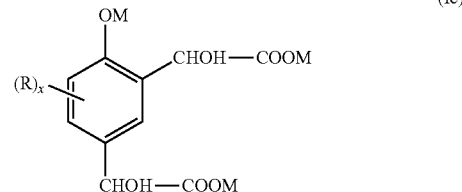
(Ic)

in said formulae, M has the meaning given in the formula (I), x is equal to 1 or 2 and the R groups, which are identical or different, represent an alkyl or alkoxy group having from 1 to 4 carbon atoms, preferably a methoxy or ethoxy group.

In the various formulae (I), (Ia), (Ib) and (Ic), M preferably represents a hydrogen atom or sodium or potassium.

The mandelic derivative of formula (I) and preferably of formulae (Ia), (Ib) and/or (Ic) is subjected to the oxidation reaction in a salified form and more preferably in a completely salified form.

If the starting mandelic substrate is not salified or insufficiently salified, the salification reaction takes place subsequently since the oxidation takes place in basic medium.

Thus, according to the process of the invention, it is possible to resort to a salified form of a mandelic derivative prepared at the time of use but it is also possible to prepare it in situ by reacting the mandelic derivative and the base.

The mandelic derivatives involved in the process of the invention are known products. They can be obtained by condensation, in an alkaline medium, of glyoxylic acid with phenol and/or its corresponding derivatives. Reference may in particular be made to WO 99/65853.

A method for the preparation of the mandelic derivatives is to carry out a condensation reaction of the phenol derivative corresponding to the formula (II) and of glyoxylic acid in the presence of an alkaline agent and optionally in the presence of a catalyst of dicarboxylic acid type:

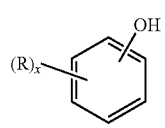
(II)

in said formula, R and x have the meanings given for the formula (I).

The condensation reaction is carried out in the presence of an alkaline agent, preferably an alkali metal hydroxide, which can be sodium hydroxide or potassium hydroxide, and, for economic reasons, sodium hydroxide is preferably chosen.

As regards the glyoxylic acid, recourse is had to an aqueous glyoxylic acid solution having a concentration varying, for example, between 15 and 70% by weight.

The glyoxylic acid is reacted with the phenolic derivative of formula (II) in excess. The molar ratio of the phenolic derivative of formula (II) to the glyoxylic acid varies between 1.0 and 4.0.

The alkali metal hydroxide solution employed has a concentration generally of between 10 and 50% by weight.

The amount of alkali metal hydroxide introduced into the reaction medium takes into account the amount necessary to salify the hydroxyl function group of the phenol derivative of formula (II) and the amount necessary to salify the carboxyl functional group of the glyoxylic acid.

The concentration of the phenolic derivative of formula (II) is preferably between 0.5 and 1.5 mol/liter.

The reaction temperature is advantageously chosen between 20° C. and 60° C.

The reaction is carried out at atmospheric pressure but under a controlled atmosphere of inert gases, preferably nitrogen or rare gases, in particular argon. Nitrogen is preferably chosen.

After bringing the phenol derivative of formula (II), the glyoxylic acid and the alkali metal hydroxide into contact, the reaction medium is kept stirred and at the temperature chosen within the abovementioned range for a variable time ranging from 1 to 10 hours.

At the end of the reaction, the separation is carried out of the mandelic derivative obtained in the salified form according to conventional separation techniques, in particular by crystallization.

A possible alternative form consists in carrying out the reaction in the presence of a catalyst of dicarboxylic acid type, preferably oxalic acid, as described in WO 99/65853.

Thus, in the process for the preparation of a hydroxyaromatic aldehyde according to the invention, an isolated mandelic derivative, such as, for example, of formula (Ia) or (Ib) or (Ic) or a crude reaction product resulting from the condensation reaction of a phenolic derivative and of glyoxylic acid as described above, which results, in this case, in a reaction mixture comprising isomers as illustrated by the formulae (Ia), (Ib) and (Ic) and optionally the reactants of the condensation reaction, when they are placed in excess during this reaction, may be involved as reaction substrate.

In accordance with the process of the invention, a mandelic derivative in a salified form and the oxidizing agent can be reacted in the presence of the catalytic system of the invention.

The concentration by weight of the mandelic substrate in the reaction medium is usually between 5% and 30% by weight, preferably between 10% and 25% by weight.

A catalytic system, the characteristic of which is to comprise at least two metal elements, is thus involved in the process of the invention. Thus, the catalytic system advantageously comprises a metal element, denoted by $M_1$, chosen from the group formed by copper, nickel, cobalt, iron and manganese, and another metal element $M_2$, which is different from $M_1$, chosen from the group formed by copper, nickel, cobalt, iron and manganese.

More preferably, the choice is made of a metal element $M_1$ chosen from the group formed by copper, nickel, cobalt and iron and of another metal element $M_2$, which is different from $M_1$, chosen from the group formed by copper, nickel, cobalt and iron.

Recourse is more preferably still had to catalytic systems comprising the following pairs of metals: cobalt/copper, cobalt/nickel, cobalt/iron, copper/iron or nickel/iron. Use may also be made of ternary mixtures of said metals. It will not be departing from the scope of the present invention to add another metal element.

The metal elements can be employed in any form. They can be provided in the metal or oxide form or in the form of a salt which may be simple or double and inorganic or organic.

Neither does the invention rule out the use of the metal elements in the form of mono- or bimetallic complexes.

More specifically, the abovementioned elements can be introduced in the form of a metal or in the form of an oxide or of a hydroxide. It is possible to resort to an inorganic salt, preferably a nitrate, sulfate, halide, silicate, carbonate or oxalate salt, or to an organic salt, preferably an acetylacetonate or carboxylate salt and more preferably still an acetate salt.

Mention may in particular be made, as examples of inorganic or organic copper compounds, as copper compounds, of cuprous and cupric bromide; cuprous iodide; cuprous and cupric chloride; basic cupric carbonate; cuprous and cupric nitrate; cuprous and cupric sulfate; cuprous sulfite; cuprous and cupric oxide; cupric hydroxide; cuprous and cupric acetate; or cupric trifluoromethylsulfonate.

The copper complexes of the salcomine type which result from the reaction of diamines, preferably ethylenediamine, and of β-dicarbonyl or hydroxycarbonyl compounds, such as, for example, 2-hydroxyacetophenone and 2-hydroxybenzaldehyde, are also suitable for the invention.

Thus, among the copper complexes of salcomine type, the complexes having the following backbone:

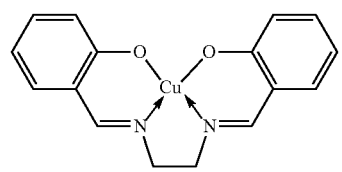

are preferred, it being possible for the benzene rings to be substituted, in particular by alkyl or alkoxy groups having from 1 to 4 carbon atoms, halogen atoms, preferably chlorine or fluorine atoms, or a nitro group.

Mention may be made, as specific examples of nickel derivatives, of nickel(II) halides, such as nickel(II) chloride, bromide or iodide; nickel(II) sulfate; nickel(II) carbonate; the salts of organic acids comprising from 1 to 18 carbon atoms, such as, in particular, acetate or propionate; nickel(II) complexes, such as nickel(II) acetylacetonate, dichlorobis(triphenylphosphine)nickel(II) or dibromobis(bipyridine)nickel(II); or nickel(0) complexes, such as bis(cycloocta-1,5-diene)nickel(0) or [bis(diphenylphospino)ethane]nickel(0).

Mention may in particular be made, as examples of cobalt-based compounds, of cobalt(II) and cobalt(III) halides, such as cobalt(II) chloride, bromide or iodide or cobalt(III) chloride, bromide or iodide; cobalt(II) and cobalt(III) sulfate; cobalt(II) carbonate or basic cobalt(II) carbonate; cobalt(II) orthophosphate; cobalt(II) nitrate; cobalt(II) and cobalt(III) oxide; cobalt(II) and cobalt(III) hydroxide; salts of organic acids comprising from 1 to 18 carbon atoms, such as, in particular, cobalt(II) and cobalt(III) acetate or cobalt(II) propionate; or cobalt(II) complexes, such as hexamminecobalt(II) chloride or hexamminecobalt(III) chloride, hexamminecobalt(II) sulfate or hexamminecobalt(III) sulfate, pentamminecobalt(III) chloride or triethylenediaminecobalt(III) chloride.

Recourse may also be had to Co(III) salen Jacobsen cobalt complexes, the formula of which is given below, or to oligomeric systems derived from said complexes and which are described by L. Aouni et al. in "Asymmetric Catalysis on Industrial Scale: Challenges, Approaches and Solutions", H. U. Blaser and E. Schmidt Eds.; Wiley, 2004, pp 165-199.

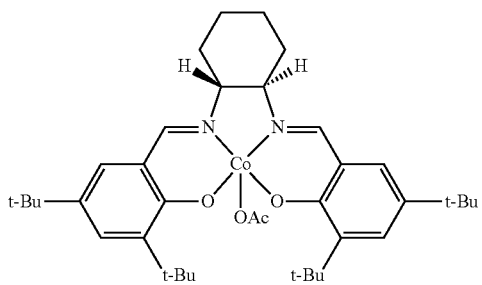

The cobalt complexes of the salcomine type which result from the reaction of diamines, preferably ethylenediamine, and of β-dicarbonyl or hydroxycarbonyl compounds, such as, for example, 2-hydroxyacetophenone and 2-hydroxybenzaldehyde, are also suitable for the invention.

Thus, among cobalt complexes of salcomine type, the complexes having the following backbone:

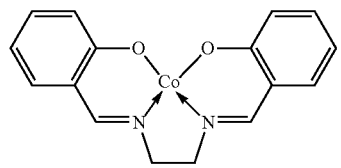

are preferred, it being possible for the benzene rings to be substituted, in particular by alkyl or alkoxy groups having from 1 to 4 carbon atoms, halogen atoms, preferably chlorine or fluorine atoms, or a nitro group.

Mention may in particular be made, as examples of manganese-based compounds, of manganese halides, for example manganese(II) chloride and manganese(III) chloride; manganese(II) bromide; manganese(II) iodide; manganese(II) chloride; manganese(II) sulfate; manganese(II) nitrate; manganese(II) oxide and manganese(III) oxide; manganese(II) hydroxide and manganese(III) hydroxide; manganese(II)acetate; or manganese(II) tartrate.

As for cobalt, manganese complexes of the salcomine type are suitable, in particular those which exhibit the following optionally substituted backbone:

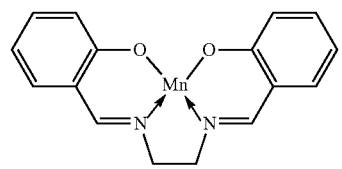

Recourse may also be had to iron-based catalytic systems, generally in the form of oxides, hydroxides or salts, such as iron(II) and iron(III) chloride, bromide, iodide or fluoride; iron(II) and iron(III) sulfate; iron(II) and iron(III) nitrate; iron(II) and iron(III) oxide; iron(II) and iron(III) hydroxide; basic iron(III) oxide; iron(II) acetate and basic iron(III)acetate; iron(III) phosphate; iron(II) and iron(III) oxalate; iron(III) acetylacetonate; or iron(II) tartrate.

Mention may be made, as sources of the various metal elements entirely well suited to the process of the invention, of at least two different compounds chosen from: cuprous chloride, cupric chloride, cuprous sulfate or cupric sulfate; nickel(II) chloride or nickel(II) sulfate; cobalt(II) chloride, cobalt(III) chloride, cobalt(II) sulfate or cobalt(III) sulfate; manganese(II) chloride or manganese(II) sulfate; or iron(III) chloride, iron(II) sulfate or iron(III) sulfate.

The catalytic system can be introduced into the process of the invention in the solid form or else in aqueous solution. By way of examples, it is specified that the concentration of the catalytic system in aqueous solution is from 5 to 20% by weight.

In accordance with the process of the invention, at least two metal elements $M_1$ and $M_2$ are involved in the catalytic system of the process of the invention.

The proportion of the metal elements in the catalytic system can vary widely.

Thus, the $M_1/M_2$ atomic ratio can range from 99.9/0.1 to 0.1/99.9 but is preferably chosen between 90/10 and 10/90 and more preferably between 70/30 and 30/70.

In the process of the invention, the amount of catalytic system to be employed with respect to the mandelic substrate to be oxidized can vary within wide limits. Thus, the amount of catalytic system, expressed by the molar ratio of the number of moles of metals $M_1+M_2$ to the number of moles of mandelic substrate present in the medium, is preferably chosen between 0.0001% and 20% and preferably between 0.01% and 0.3%.

According to the process of the invention, the oxidation is carried out in an aqueous medium comprising, in solution, a basic agent and more particularly ammonium hydroxide or alkali metal or alkaline earth metal bases, among which may be mentioned alkali metal and alkaline earth metal hydroxides, such as sodium hydroxide, potassium hydroxide, cesium hydroxide, lithium hydroxide and barium hydroxide, or alkali metal and alkaline earth metal carbonates, preferably sodium carbonate or potassium carbonate.

Recourse may also be had to organic bases, such as quaternium ammonium hydroxides, for example tetraalkylammonium or trialkylbenzylammonium hydroxides, the alkyl groups of which, which are identical or different, represent a linear or branched alkyl chain preferably having from 1 to 6 carbon atoms.

The choice will preferably be made of tetramethylammonium hydroxide, tetraethylammonium hydroxide, tetrabutylammonium hydroxide or trimethylbenzylammonium hydroxide.

For economic reasons, the base chosen is preferably sodium hydroxide or potassium hydroxide.

The alkali metal hydroxide solution employed has a concentration generally of between 5 and 50% by weight. The concentration of the starting solution is not critical. However, it is preferable to resort to a more concentrated solution with a concentration varying between 30 and 50% by weight.

The amount of base employed, expressed as molar percentages with respect to the mandelic substrate, generally varies between 80 and 300% of the stoichiometric amount.

As mentioned above, the mandelic substrate is oxidized using an oxidizing agent in basic medium and in the presence of a solid catalytic system or catalytic system in aqueous solution defined above.

Mention may in particular be made, as oxidizing agents capable of being employed in the process of the invention, of hydrogen peroxide, peracids, such as peracetic acid, or hydroperoxides, such as tert-butyl hydroperoxide, cyclohexyl hydroperoxide or cumyl hydroperoxide.

Recourse is preferably had, among the above-mentioned oxidizing agents, to hydrogen peroxide.

Hydrogen peroxide is advantageously employed in its commercial form, namely an aqueous solution, the concentration of which generally varies between 30% and 70%.

The amount of oxidizing agent introduced can vary widely. Generally, it is equal to the stoichiometric amount, indeed even in a slight excess of 20% with respect to the stoichiometric amount.

Although a chemical oxidizing agent can be used, recourse is preferably had to molecular oxygen or a gas comprising it. This gas can be pure oxygen or oxygen diluted with an inert gas, for example nitrogen or a rare gas, preferably argon. Recourse may thus be made to air.

The amount of oxygen to be employed is not critical insofar as it is such that neither the feed gases nor a possible gas phase capable of appearing in the reaction region occurs within the range of explosive compositions, taking into consideration the other reaction parameters or conditions chosen. The amount of oxygen is at least equal to the stoichiometric amount of the reaction, with regard to the substrate to be oxidized. The ratio of the number of moles of oxygen to the number of moles of mandelic substrate is at least 0.5. The upper limit is not critical. Said ratio is advantageously chosen between 0.5 and 50.

The reaction pressure varies between atmospheric pressure and approximately 20 bar. A pressure between 1 and 10 bar is preferred.

The process of the invention can be carried out at atmospheric pressure, pure oxygen being bubbled through.

Another alternative form of the invention consists in operating under pressure in an autoclave. In this case, dilute oxygen, preferably air, is employed under a pressure advantageously of the order of 1 to 10 bar.

The mixture is subsequently stirred at the desired temperature until an amount of oxygen corresponding to that necessary to convert the mandelic group to a formyl group has been consumed.

The reaction temperature to be adopted varies according to the thermal stability of the products to be prepared.

In accordance with the invention, the temperature is preferably chosen within a temperature range extending from 50° C. to 95° C.

It should be noted that the reaction is generally carried out in an aqueous medium but the invention does not rule out the use of an organic solvent provided that the reaction temperature is greater, for example, than 100° C. Mention may be made, as more particular examples of organic solvents, of dimethyl sulfoxide or dimethylformamide.

From a practical viewpoint, the mandelic substrate, the catalytic system and the basic solution and then the oxidizing agent are charged to the reactor.

In the case where the oxidizing agent is in liquid form, it is introduced at the same time as the other reactants.

When the oxidizing agent is in the gaseous form, the reaction medium is stirred and heated to the chosen reaction temperature and then molecular oxygen or gas comprising it is then conveyed.

At the end of the reaction, a hydroxyaromatic aldehyde corresponding to the formula (III):

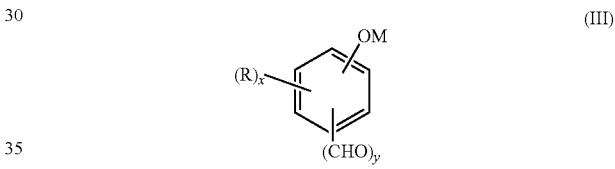

in said formula, R, M, x and y have the meanings given above, is obtained in the reaction medium.

The aldehyde formed is recovered according to conventional separation techniques, for example extraction using an appropriate solvent or distillation.

The process of the invention applies particularly to the preparation of the following hydroxyaromatic aldehydes: vanillin, ethyl vanillin or protocatechualdehyde.

The oxidation process according to the invention results in the production of the hydroxyaromatic aldehyde with a good reaction yield often of greater than 90% but it is particularly advantageous as it makes it possible to significantly increase the selectivity of the reaction, as is demonstrated in the following examples.

Various implementational examples of the invention are given by way of illustration.

Examples 1 to 9 relate to the preparation of vanillin according to the process of the invention.

Examples a to f are comparative tests employing a catalytic system comprising only a single metal element.

In the examples, the selectivity (YD) corresponds to the ratio of the number of moles of product formed (aldehyde) to the number of moles of mandelic substrate converted.

EXAMPLES

The procedure used in the various examples 1 to 9 is given below.

The oxidation reaction is carried out in a reactor made of stainless steel 316L (or of glass) which is equipped with a mechanical stirring system, baffles, an oxygen or air inlet regulated by a flow meter and a vertical reflux condenser.

Either 4-hydroxy-3-methoxymandelic acid ("APM") or a crude reaction product comprising 25% by weight of APM (denoted by "Crude product"), which results from a condensation reaction between glyoxylic acid and guaiacol carried out according to the teaching of the state of the art (WO 99/65853), is charged to the reactor.

The catalytic system defined below in the examples is charged with stirring and then the medium is heated to 50° C.

The appropriate amount of a 50% aqueous sodium hydroxide solution, corresponding to the amount required by the stoichiometry of the reaction, is added.

The medium is then heated to 80° C. and oxygen is introduced with a flow rate of the order of 1.6 l/h.

The reaction is continued until oxygen is no longer being consumed.

The chemical performance of the reaction is determined by liquid chromatography.

Example 1

The procedure given above is reproduced while employing a crude reaction product as defined and a catalytic system comprising $CoCl_2.6H_2O$ and $CuSO_4.5H_2O$, respectively employed in an amount, expressed as molar percentage of APM, of 0.125 and 0.125.

After reacting for 30 minutes, a selectivity of the reaction for vanillin of 98% is obtained.

Example 2

The procedure given above is reproduced while employing a crude reaction product as defined and a catalytic system comprising $CoCl_2.6H_2O$ and $CuSO_4.5H_2O$, respectively employed in an amount, expressed as molar percentage of APM, of 0.028 and 0.267.

After reacting for 30 minutes, a selectivity of the reaction for vanillin of 97% is obtained.

Example 3

The procedure given above is reproduced while employing APM and a catalytic system comprising $CoCl_2.6H_2O$ and $CuSO_4.5H_2O$, respectively employed in an amount, expressed as molar percentage of APM, of 0.042 and 0.040.

After reacting for 30 minutes, a selectivity of the reaction for vanillin of 98% is obtained.

Example 4

The procedure given above is reproduced while employing APM and a catalytic system comprising $CoCl_2.6H_2O$ and $CuSO_4.5H_2O$, respectively employed in an amount, expressed as molar percentage of APM, of 0.010 and 0.005.

After reacting for 30 minutes, a selectivity of the reaction for vanillin of 95% is obtained.

Example 5

The procedure given above is reproduced while employing APM and a catalytic system comprising $CoCl_2.6H_2O$ and $CuSO_4.5H_2O$, respectively employed in an amount, expressed as molar percentage of APM, of 0.005 and 0.010.

After reacting for 30 minutes, a selectivity of the reaction for vanillin of 97% is obtained.

Example 6

The procedure given above is reproduced while employing a crude reaction product as defined and a catalytic system comprising $CoCl_2.6H_2O$ and $NiCl_2.6H_2O$, respectively employed in an amount, expressed as molar percentage of APM, of 0.125 and 0.132.

After reacting for 30 minutes, a selectivity of the reaction for vanillin of 100% is obtained.

Example 7

The procedure given above is reproduced while employing a crude reaction product as defined and a catalytic system comprising $CoCl_2.6H_2O$ and $Fe_2(SO_4)_3$, respectively employed in an amount, expressed as molar percentage of APM, of 0.125 and 0.117.

After reacting for 30 minutes, a selectivity of the reaction for vanillin of 100% is obtained.

Example 8

The procedure given above is reproduced while employing a crude reaction product as defined and a catalytic system comprising $CuSO_4.5H_2O$ and $Fe_2(SO_4)_3$, respectively employed in an amount, expressed as molar percentage of APM, of 0.125 and 0.120.

After reacting for 30 minutes, a selectivity of the reaction for vanillin of 100% is obtained.

Example 9

The procedure given above is reproduced while employing a crude reaction product as defined and a catalytic system comprising $NiCl_2.6H_2O$ and $Fe_2(SO_4)_3$, respectively employed in an amount, expressed as molar percentage of APM, of 0.125 and 0.128.

After reacting for 30 minutes, a selectivity of the reaction for vanillin of 100% is obtained.

Comparative Tests a to d

By way of comparison, a series of tests is carried out while employing only a single metal element.

On comparing the results obtained in the examples of the invention and the various comparative tests, a better performance of the catalytic systems of the invention comprising two metal elements is recorded in terms of selectivity.

Test a

The procedure given above is reproduced while employing a crude reaction product as defined and a catalytic system comprising $CoCl_2.6H_2O$, employed in an amount, expressed as molar percentage of APM, of 0.250.

After reacting for 30 minutes, a selectivity of the reaction for vanillin of 86% is obtained.

An improvement in the coloring of the reaction medium, which is light orange in example 1 compared with a black color obtained in this test, is observed.

Test b

The procedure given above is reproduced while employing APM and a catalytic system comprising $CoSO_4.7H_2O$, employed in an amount, expressed as molar percentage of APM, of 0.220.

After reacting for 30 minutes, a selectivity of the reaction for vanillin of 82% is obtained.

Test c

The procedure given above is reproduced while employing a crude reaction product as defined and a catalytic system comprising CuSO$_4$.5H$_2$O, employed in an amount, expressed as molar percentage of APM, of 0.250.

After reacting for 30 minutes, a selectivity of the reaction for vanillin of 68% is obtained.

An improvement in the coloring of the reaction medium, which is light orange in example 1 compared with a black color obtained in this test, is observed.

Test d

The procedure given above is reproduced while employing a crude reaction product as defined and a catalytic system comprising Fe$_2$(SO$_4$)$_3$, employed in an amount, expressed as molar percentage of APM, of 0.215.

After reacting for 30 minutes, a selectivity of the reaction for vanillin of 89% is obtained.

What is claimed is:

1. A process for the preparation of a hydroxyaromatic aldehyde via oxidation of the corresponding mandelic derivative in basic medium, comprising conducting such oxidation of said mandelic derivative in the presence of a catalytic system which comprises at least two metal elements M$_1$ and M$_2$ selected from the group consisting of copper, nickel, cobalt, iron and manganese.

2. The process as defined by claim 1, wherein said mandelic derivative substrate has the following formula (I):

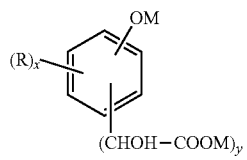

in which:
  M is a hydrogen atom and/or a metal cation of Group Ia of the Periodic Table or an ammonium cation,
  R is a hydrogen atom or one or more identical or different substituents,
  y is a number equal to 1 or 2,
  x, the number of substituents on a ring, is a number less than or equal to 4,
  with the proviso that when x is greater than 1, two R groups situated on two adjacent carbon atoms together form, with the carbon atoms from which they depend, a saturated, unsaturated or aromatic ring member having from 5 to 7 atoms and optionally including one or more heteroatoms.

3. The process as defined by claim 2, wherein the mandelic derivative substrate has the formula (I) in which the R groups, which may be identical or different, are each a hydrogen atom, an alkyl, alkenyl, alkoxy, hydroxyalkyl, alkoxyalkyl, cycloalkyl, aryl or arylalkyl radical, a hydroxyl group, a nitro group, a halogen atom, a halo- or perhaloalkyl group, a carboxyl group or an amino group which is unsubstituted or substituted by one or two alkyl radical or phenyl groups and, when x is greater than 1, two R groups situated on two adjacent carbon atoms can be bonded to one another via an alkylene, alkenylene or alkenylidene radical having from 3 to 5 carbon atoms to form a saturated, unsaturated or aromatic ring member having from 5 to 7 atoms, with the proviso that one or more carbon atoms may be replaced by a heteroatom.

4. The process as defined by claim 2, wherein the mandelic derivative substrate has the formula (I) in which the R groups, which may be identical or different, are each:
  a hydrogen atom,
  a hydroxyl group,
  a linear or branched alkyl radical having from 1 to 6 carbon atoms, and selected from among the methyl, ethyl, n-propyl, isopropyl, n-butyl, isobutyl, sec-butyl and tert-butyl radicals,
  a linear or branched alkenyl radical having from 2 to 6 carbon atoms,
  a linear or branched alkoxy radical having from 1 to 6 carbon atoms, and selected from among the methoxy, ethoxy, n-propoxy, isopropoxy, n-butoxy, isobutoxy, sec-butoxy and tert-butoxy radicals,
  a phenyl group, and
  a fluorine, chlorine or bromine atom.

5. The process as defined by claim 2, wherein the mandelic derivative substrate has the formula (I) in which y is equal to 1 and x is equal to 0, 1 or 2.

6. The process as defined by claim 2, wherein the mandelic derivative substrate has the formula (I) in which a glycolic substituent is in the ortho or para position with respect to a hydroxyl group.

7. The process as defined by claim 1, wherein the mandelic derivative substrate comprises a crude reaction mixture resulting from the condensation, in an alkaline medium, of glyoxylic acid with a corresponding phenolic derivative.

8. The process as defined by claim 7, wherein said crude reaction mixture comprises the compounds having the following formulae:

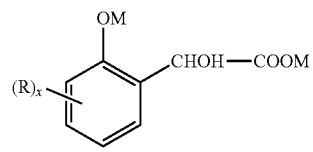

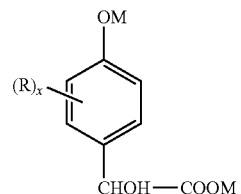

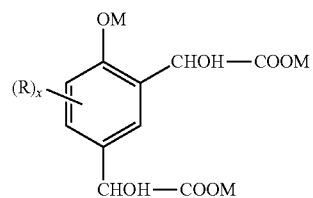

in said formulae, M has the definition given in the formula (I), x is equal to 1 or 2 and the R groups, which may be identical or different, are each an alkyl or alkoxy radical having from 1 to 4 carbon atoms.

9. The process as defined by claim 1, wherein the mandelic derivative substrate is selected from among:
  4-hydroxy-3-methoxymandelic acid,
  3-ethoxy-4-hydroxymandelic acid,
  3,4-dihydroxymandelic acid,
  2,4-dihydroxymandelic acid,
  2-hydroxy-5-methylmandelic acid,
  2-hydroxy-5-methoxymandelic acid,
  4-hydroxy-3-chloromandelic acid,
  4-hydroxy-3-bromomandelic acid,
  4-hydroxy-3-fluoromandelic acid, 4-hydroxymandelic acid,
4-hydroxy-3-methoxy-5-methylmandelic acid, and
2-hydroxy-2-(1-hydroxynaphth-2-yl)acetic acid.

10. The process as defined by claim 1, wherein the concentration by weight of the mandelic derivative substrate in the reaction medium ranges from 5% to 30% by weight.

11. The process as defined by claim 1, wherein the metal elements are introduced in the form of a metal or in the form of an oxide or of a hydroxide, in the form of an inorganic salt selected from among a nitrate, sulfate, halide, silicate, carbonate or oxalate salt, or of an organic salt selected from among an acetylacetonate or carboxylate salt or an acetate salt, or in the form of a mono- or bimetallic complex.

12. The process as defined by claim 1, wherein copper, cobalt and manganese are introduced in the form of complexes of salcomine type and cobalt also in the form of a Co(III)salen Jacobsen complex.

13. The process as defined by claim 1, wherein the metal elements are introduced via at least two different compounds selected from among cuprous chloride, cupric chloride, cuprous sulfate or cupric sulfate; nickel(II) chloride or nickel(II) sulfate; cobalt(II) chloride, cobalt(III) chloride, cobalt(II) sulfate or cobalt(III) sulfate; manganese(II) chloride or manganese(II) sulfate; or iron(III) chloride, iron(II) sulfate or iron(III) sulfate.

14. The process as defined by claim 1, wherein the catalytic system is introduced in the solid state or else in aqueous solution.

15. The process as defined by claim 1, wherein the catalytic system comprises an $M_1/M_2$ pair selected among the following pairs of metals: cobalt/copper, cobalt/nickel, cobalt/iron, copper/iron or nickel/iron.

16. The process as defined by claim 1, wherein the proportion of the metal elements in the catalytic system is such that the $M_1/M_2$ atomic ratio varies from 99.9/0.1 to 0.1/99.9.

17. The process as defined by claim 1, wherein the amount of catalytic system employed, expressed by the molar ratio of the number of moles of metals $M_1$ and $M_2$ to the number of moles of mandelic derivative substrate present in the reaction medium, ranges from 0.0001% to 20%.

18. The process as defined by claim 1, wherein the oxidation is carried out in an aqueous medium comprising, in solution, a basic agent selected from among ammonium hydroxide, alkali metal or alkaline earth metal hydroxides, selected from among sodium hydroxide, potassium hydroxide, cesium hydroxide, lithium hydroxide and barium hydroxide, and sodium carbonate or potassium carbonate, or quaternium ammonium hydroxides.

19. The process as defined by claim 1, wherein the reaction is carried out in the presence of molecular oxygen or gas comprised thereof.

20. The process as defined by claim 1, wherein the temperature of the oxidation reaction ranges from 50° C. to 95° C.

21. The process as defined by claim 1, wherein the reaction pressure ranges from atmospheric pressure to approximately 20 bar.

22. The process as defined by claim 1, wherein the reaction is carried out in an aqueous medium or in an organic solvent.

23. The process as defined by claim 1, wherein the mandelic derivative substrate, the catalytic system and the basic solution are charged into the reactor, the reaction medium is adjusted to the selected reaction temperature and then a stream of oxygen or gas comprised thereof is bubbled therethrough.

24. The process as defined by claim 1, wherein the product hydroxyaromatic aldehyde obtained is vanillin, ethyl vanillin or protocatechualdehyde.

* * * * *